United States Patent
Organ et al.

(12)

(10) Patent No.: US 10,585,071 B2
(45) Date of Patent: Mar. 10, 2020

(54) MULTIDIMENSIONAL PEAK PURITY ANALYSIS

(71) Applicants: Michael Organ, Ottawa (CA); Debasis Mallik, Newmarket (CA)

(72) Inventors: Michael Organ, Ottawa (CA); Debasis Mallik, Newmarket (CA)

( * ) Notice: Subject to any disclaimer, the term of this patent is extended or adjusted under 35 U.S.C. 154(b) by 400 days.

(21) Appl. No.: 15/348,311

(22) Filed: Nov. 10, 2016

(65) Prior Publication Data

US 2018/0128795 A1     May 10, 2018

Related U.S. Application Data

(60) Provisional application No. 62/285,837, filed on Nov. 12, 2015.

(51) Int. Cl.
 *G01N 30/46* (2006.01)
(52) U.S. Cl.
 CPC ......... *G01N 30/468* (2013.01); *G01N 30/463* (2013.01)
(58) Field of Classification Search
 CPC .................. G01N 30/463; G01N 30/468
 See application file for complete search history.

(56) References Cited

U.S. PATENT DOCUMENTS

| | | | | |
|---|---|---|---|---|
| 6,802,967 B2* | 10/2004 | Masuda | ............... | G01N 30/463 210/198.2 |
| 8,101,422 B2* | 1/2012 | Srinivasan | ........... | G01N 30/463 205/789 |
| 2006/0157647 A1* | 7/2006 | Siuzdak | ............... | G01N 30/463 250/288 |

* cited by examiner

*Primary Examiner* — David Z Huang

(57) ABSTRACT

A multidimensional chromatographic assembly includes a pump module, an injector, a path selector device, an array of chromatographic media, a loop selector device and a detector assembly for receiving at least a portion of an analyte stream and flowing the injected stream into the detector assembly via a chromatographic medium (the first dimension). At least a portion of the analyte of interest is then channeled into a chromatographic medium of interest (the second dimension) and re-circulated through the detector assembly. The iteration (multidimension) is continued until all aspects of the chromatogram and the peaks are judged to be analyzed. The entire process is controlled from a computer and the results are collected to make decisions on the analytical and the process controls.

7 Claims, 25 Drawing Sheets

MULTIDIMENSIONAL PEAK PURITY ANALYSIS

CROSS REFERENCE TO RELATED APPLICATION(S)

This application claims the benefit of 35 USC 119 based on the priority of co-pending U.S. Provisional Patent Application 62/285,837, filed Nov. 12, 2015, this application being incorporated herein by reference.

FIELD

The disclosure relates to multidimensional chromatographic analysis, such as the one used in heart-cut methods. More specifically, the disclosure relates to a multidimensional chromatographic analysis which may be applied to the iterative analyses of selected peak(s) for purity measurements, also to methods and devices for trapping and re-analyzing target peak(s), and for recording outcomes in order to implement intelligent run-controls. The disclosure is specifically intended for applications, in which the peak purity analyses from a second dimension analysis needs to be validated from a third or higher order multidimensional analysis. The ability to re-examine the outcome of the two-dimensional analysis in higher dimensions is critical in various areas including, but not restricted to, study of on-column sample degradation or chiral analyses.

BACKGROUND

U.S. Pat. No. 8,101,422 (Srinivasan et al.) purports to disclose a multidimensional ion chromatography apparatus for analyzing a sample in the first dimension and then transferring a selected portion of the eluent to a second dimension for analysis. The system is capable of concentrating or purifying certain components prior to the second dimension injection. The capability of their analysis is limited to two dimensions. Additionally, more than one set of pumps were used to support their claims for the two-dimensional analysis. Extension of the technology to higher dimensions could require multiple number of liquid moving devices (pumps) and more than one detector.

U.S. Pat. No. 6,802,967 (Masuda et al.) purports to disclose a multi-dimensional liquid chromatography system for storing the analyte(s) from the first dimension run and re-injecting the analyte(s) into the second dimension column(s). The system is also capable of de-salting the sample while in storage using solvents other than the mobile phase solvents. Each dimension has a dedicated detection device. The design is equipped with two detectors and consequently, can not be extended beyond two dimensions for analytical applications.

US Pat. No. 20060157647 A1 (Siuzdak et al.) purports to disclose a multidimensional liquid chromatography system for moving a sample chromatographed from the first dimension alternatingly through a set of two columns for mass spectrometric and NMR spectroscopic analyses. According to their claims, a first dimension column was alternatingly set in fluid communications with two different detectors and the data obtained from both channels are claimed to constitute a dataset for a three-dimensional analysis. The setup is not capable of re-injecting an analyte from the second dimension into the third dimension.

SUMMARY

The following summary is intended to introduce the reader to various aspects of the applicant's teaching, but not to define any invention.

The term "heart-cut" used in this summary is intended to define a process of isolating at least a portion of an analyte and storing the isolated analyte in a liquid holding device for an intended period of time. The process of isolating is also synonymously termed as "trapping", "parking", "capturing" or "storing" in this summary.

The term "peak" used in this summary represents the analyte of interest in the chromatographed output display (chromatogram). When a portion of the chromatophed stream is channeled into a liquid holding device and isolated (trapped or parked or captured or stored), the physical embodiment of the liquid sample can be also termed as "peak". For example, "a peak is stored in a liquid holding device" means an analyte of interest is isolated in a liquid holding device and the selection of the liquid analyte was based on its appearance (a signal) in the previous dimension chromatogram as a peak.

According to one aspect, a multidimensional chromatographic assembly comprises fluid channeling device(s) (e.g., one or a set of multiposition valves) for receiving at least one injection and dispensing the injected sample to a fluid path comprised of path selector device(s) (e.g., one or a set of multiposition valve(s) or stream selector valve(s)) for channeling the analyte(s) into a particular chromatographic medium of interest using a pump or a set of pumps, or other such devices that can move fluid. A detector or a set of detectors is in fluid communication with the fluid moving device(s). The multiposition valve is capable of trapping at least a portion of the analyte peak(s) in selected fluid holding device(s), such as loop(s), chip(s) and other containers of fluid, and injecting into the subsequent chromatographic media or diverting the peak(s) to waste.

In some embodiments, the multidimensional chromatographic assembly may further comprise a set of valves downstream of the device described above, and the entire valve assembly including the valves downstream of the detector assembly may constitute the multidimensional chromatographic assembly. The valve may be movable to divert a peak away from the primary chromatorgraphic path or to inject the peak back into a chromatographic path for further analyses. The valve may be configured to divert the peak without de-pressurizing any of the fluid paths that are designed to communicate with the valve channels. The valve may be a multi-port multi-position valve, which is movable to direct peak(s) to fluid holding devices (e.g., loops), isolate the peak(s) from the active stream, store the peak(s), and divert the peak(s) either to an analytical stream or to waste at a chosen time.

In some embodiments, the valve assembly comprises an inline cartridge or a set of cartridges equipped with purifying media arranged in parallel or in series. The cartridge assembly may comprise devices for the pre-injection sample preparatory events.

In some embodiments, the detector assembly is downstream of the primary chromatographic path (the first dimension) and upstream of the other chromatographic paths (subsequent dimensions).

In some embodiments, the multidimensional chromatographic assembly may comprise additional detectors in parallel or in series to the primary detector assembly. In some embodiments, the detectors may not be in direct contact with each other, but remain in series via indirect fluid paths and may be in fluid communication via other devices.

According to another aspect, a method for the multidimensional analysis comprises a) injecting an analyte to a primary chromatographic media (the first dimension); b) analyzing the injected sample from the first dimension; c)

trapping at least a portion of a peak of interest in at least one fluid holding device (e.g., a loop) thereby parking it; d) flowing the parked (i.e., heart-cut) peak into a subsequent path at a chosen time; and d) analyzing the heart-cut peak from the subsequent dimension.

In some embodiments, the method may further comprise e) trapping the analyzed peak from the second dimension and subsequently heart-cut at least a portion of a target peak using at least one of the downstream valves for a tertiary analysis. Step e) may comprise moving a multi-port, multi-position valve to isolate a peak from the secondary analysis stream, and divert the peak(s) to a tertiary chromatographic stream.

In some embodiments, the method may further comprise f) programming at least one of the heart-cut events based on a pre-determined time or based on the advance detector response or an external event (e.g, a signal). Step f) may comprise moving a multi-port multi-position valve to isolate a peak from the primary analysis stream, and divert the peak to a higher order chromatographic stream.

BRIEF DESCRIPTION OF THE DRAWINGS

The drawings included herewith are for illustrating various examples of articles, methods, and devices of the present specification and are not intended to limit the scope of what is taught in any way. In the drawings.

SUMMARY OF INVENTION

The chromatographic assembly according to the subject of invention includes a design and a method to isolate a fluid stream in a liquid holding device and to re-inject at least a portion of the parked fluid from the liquid holding device to a chromatographic medium using a multidimensional chromatography assembly comprising an injector, a fluid moving device, a fluid channeling device (e.g., a loop selector device), a path selector device, and a detector assembly. The entire setup and the method are capable of trapping and re-injecting any portion of the chromatographed fluid stream into the same or different chromatographic media multiple (more than two) times in order to perform a multi-dimensional analysis.

DETAILED DESCRIPTION

Various devices or processes will be described below to provide an example of an embodiment of the invention. No embodiment described below limits any claimed invention and any claimed invention may cover methods or devices that differ from those described below. The claimed invention is not limited to devices or methods having all of the features of any one device or method described below or to features common to multiple or all of the devices described below. It is possible that a device or method described below is not an embodiment of any exclusive right granted by issuance of this patent application. Any invention disclosed in a device or method described below and for which an exclusive right is not granted by issuance of this patent application may be the subject matter of another protective instrument, for example, a continuing patent application, and the applicants, inventors or owners do not intend to abandon, disclaim or dedicate to the public any such invention by its disclosure in this document.

Figure 1:
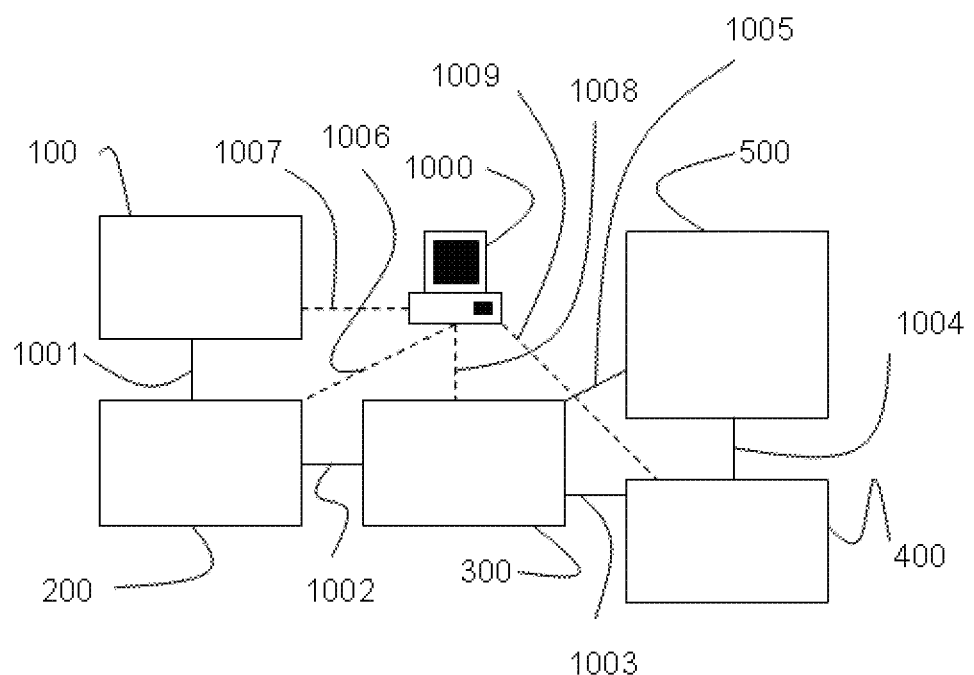
FIG. 1 is a flow diagram of an example of the multidimensional chromatographic assembly.

Referring to FIG. 1, an embodiment of the multidimensional chromatographic assembly is shown. The chromatographic assembly generally includes a pump module 100, an injector 200, a path selector and a fluid channeling device (e.g., a loop selector) 300, a detector assembly 400, an array of chromatographic media 500, and a computer 1000.

Referring still to FIG. 1, the pump module 100 is connected to the injector 200 via a fluid path 1001. The injector 200 is connected to the path selector and the loop selector device 300 via a fluid path 1002.

Referring still to FIG. 1, the path selector and the loop selector device 300, the chromatographic media array 500, and the detector assembly 400 are inter-connected via fluid paths of type 1003, 1004 and 1005.

Referring still to FIG. 1, the computer 1000 can communicate with the pump module 100, injector 200, the path selector and the loop selector devices 300, the detector assembly 400 via 1007, 1006, 1008 and 1009 communication cables respectively.

Figure 2:
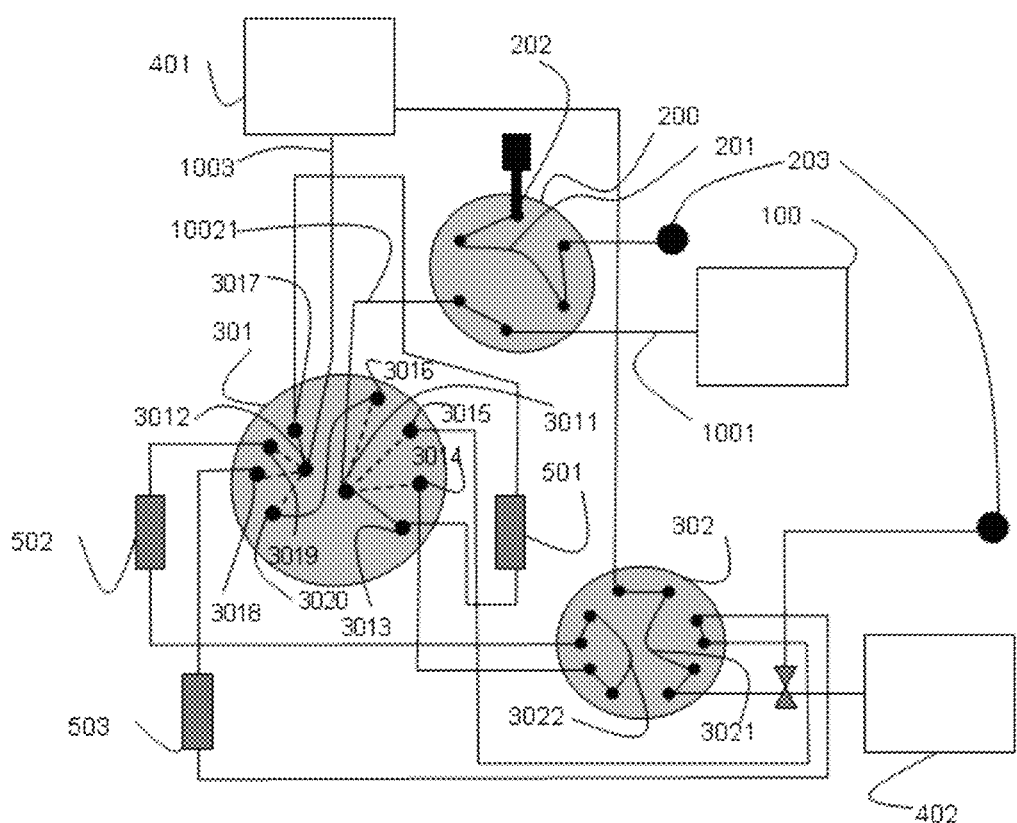
FIG. 2 is a flow diagram of the devices of the multidimensional chromatographic assembly of FIG. 1.

Referring to FIG. 2, the injector 200 includes an injection loop 201, into which at least a portion of an analyte is injected. In the embodiment shown, the loop 201 is in fluid communication with the injector syringe via port 202. In some embodiments, the other end of the fluid path is an waste port 203.

Figure 3A:
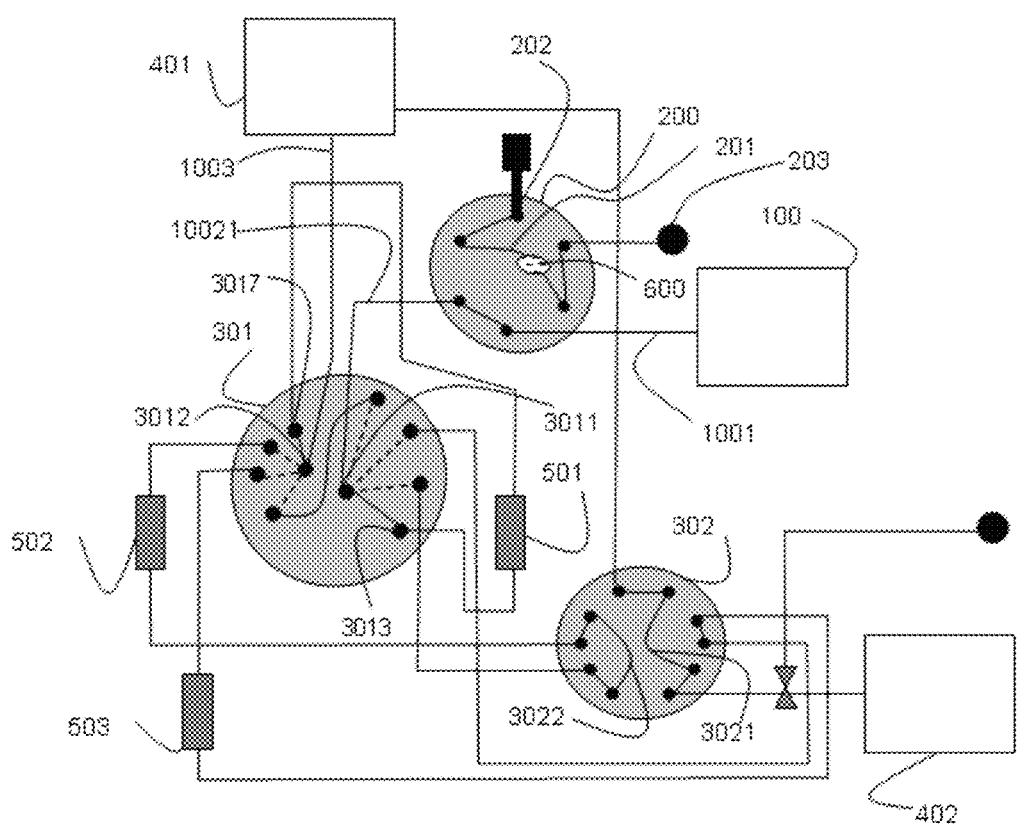
FIG. 3A is a flow diagram of the devices of the multidimensional chromatographic assembly of FIG. 1, showing an example of the individual valve positions for the first dimension injection; the analyte is injected into a fluid holding device (e.g., a loop)

Referring to FIG. 3A, the loop 201 is in fluid communication with the injector syringe via port 202 and the injector 200 receives at least a portion of an injected analyte 600 in the loop 201. In some embodiments, the other end of the fluid path is an waste port 203. In alternate embodiments, the loop 201 may receive more than one injection for a single analysis.

Figure 3B:
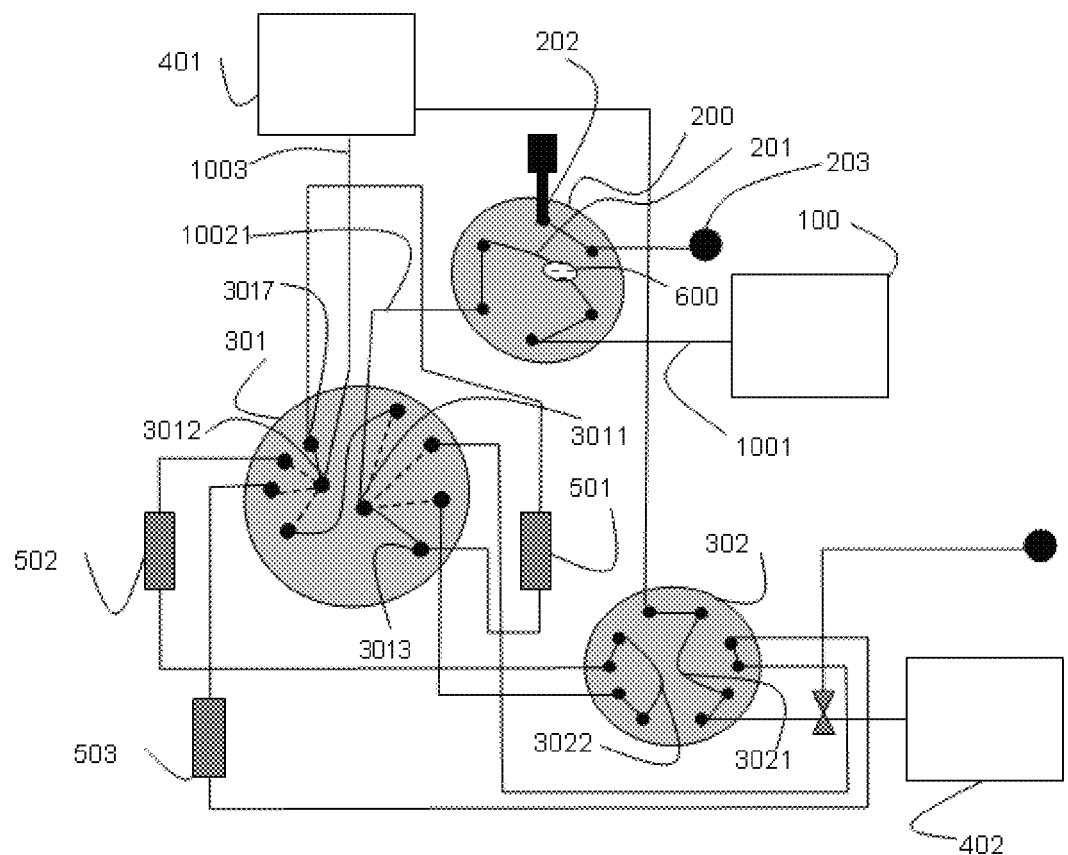
FIG. 3B is a flow diagram of the devices of the multidimensional chromatographic assembly of FIG. 1, showing an example of the individual valve positions for the first dimension injection; the analyte is in the loop and is in fluid communication to a liquid moving device (e.g., a pump or a set of pumps)

Referring to FIG. 3B, the injector 200 is further capable of switching to a second position, in which the injection port 202 is not in fluid communication with the loop 201. The loop 201 is in fluid communication with the pump module 100 via 1001 and with the path selector device 301 via 10021.

Referring still to FIG. 3B, in some embodiments, the injector may assume a position where the loop 201 establishes a temporary fluid communication with either the pump module 100 or the path selector device 301 before connecting to both.

Referring back to FIG. 2, the fluid stream, containing the analyte(s) from the injection, is dispensed from the injector 200 to the path selector device 301 and is directed to an appropriate fluid stream. In the embodiment shown, the path selector device 301 comprises an inlet 3011 and an outlet 3012, which can establish fluid communications to one of the ports between 3013 and 3016 and between 3017 and 3020 respectively.

Referring still to FIG. 2, in the embodiment shown, the path selector device 301 forms a fluid connection between a set of inlet and outlet port pairs, e.g., 3013 and 3017 or 3014 and 3018 or 3015 and 3019 or 3016 and 3020.

Referring still to FIG. 2, in the embodiment shown, a part of the chromatographic media array 500 (specifically, 501) is situated between the inlet port 3011 and the outlet port 3012 via the ports 3013 and 3017, respectively.

In some embodiments, the path selector device 301 may be operated in a way so as to establish fluid communications between a specific pair of ports (e.g., 3013 and 3017) not simultaneously, but in sequence.

Referring still to FIG. 2, in the embodiment shown, outlet 3012 is in fluid communication with the detector device 401 via 1003.

Referring back to FIG. 1, the detector assembly 400 may include additional detectors capable of accepting analyte(s) in parallel or in series. In some embodiments, the detector arrays may not be in direct fluid communications, but in indirect communications via a set of devices. In the embodiment shown in FIG. 2, a second detector device 402 is connected in series to the first detector device 401 via the loop selector device 302.

Referring back to FIG. 1, the detector assembly 400 may use technologies to detect analytes without altering the state of the analyte (i.e., non-disruptive). In alternate embodiments, the detector 400 may alter the state of the analyte in the process of detection. In those embodiments, analysis from the subsequent dimensions may only describe the state of altered species.

Referring still to FIG. 2, in the embodiment shown, the detector device 401 is connected to another part of the fluid channeling device (the loop selector device) 302. In the embodiment shown, the path selector device 301 establishes a fluid communication between the outlet 3012 and the loop 3021 via the detector device 401. In alternate embodiments, the outlet 3012 can also establish a fluid communication with the loop 3022 through the detector device 401, if and when the loop selector device 302 is appropriately rotated to a new position, either in one or more than one steps.

Referring still to FIG. 2, in some embodiments, the loop selector device 302 may be rotated in a way so as to establish fluid communications between the pump module 100 (via the injector 200, the path selector device 301 and the detector device 401) and the chromatographic media 500 (specifically, 502 or 503) not simultaneously, but in sequence.

Referring still to FIG. 2, in the embodiment shown, the loop 3021 is in fluid communication with the chromatographic medium 501 (via the injector 200, the path selector device 301 and the detector device 401) and the loop 3022 is in fluid communication with the chromatographic medium 502. In an alternate embodiment, the loop 3021 can establish a fluid communication between the pump module 100 and a part of the chromatographic media array 500 (specifically, 503) via the injector 200, the path selector and the loop selector devices 300, and the detector assembly 400. In that embodiment, the loop 3022 establishes a fluid communication with the chromatographic medium 501.

Referring to still to FIG. 2, in some embodiments, the path selector device 301 may have additional ports (3016 and 3020) connected by a liquid holding device(s), such as the loop(s), chip(s) and others. When the path selector device 301 rotated appropriately, the pump module 100 may establish a fluid communication with the ports 3016 and 3020 to populate the relevant flow-paths (e.g., 1001, 10021 and others) with a desired mobile phase condition suitable for the next chromatographic run.

Figure 4A:
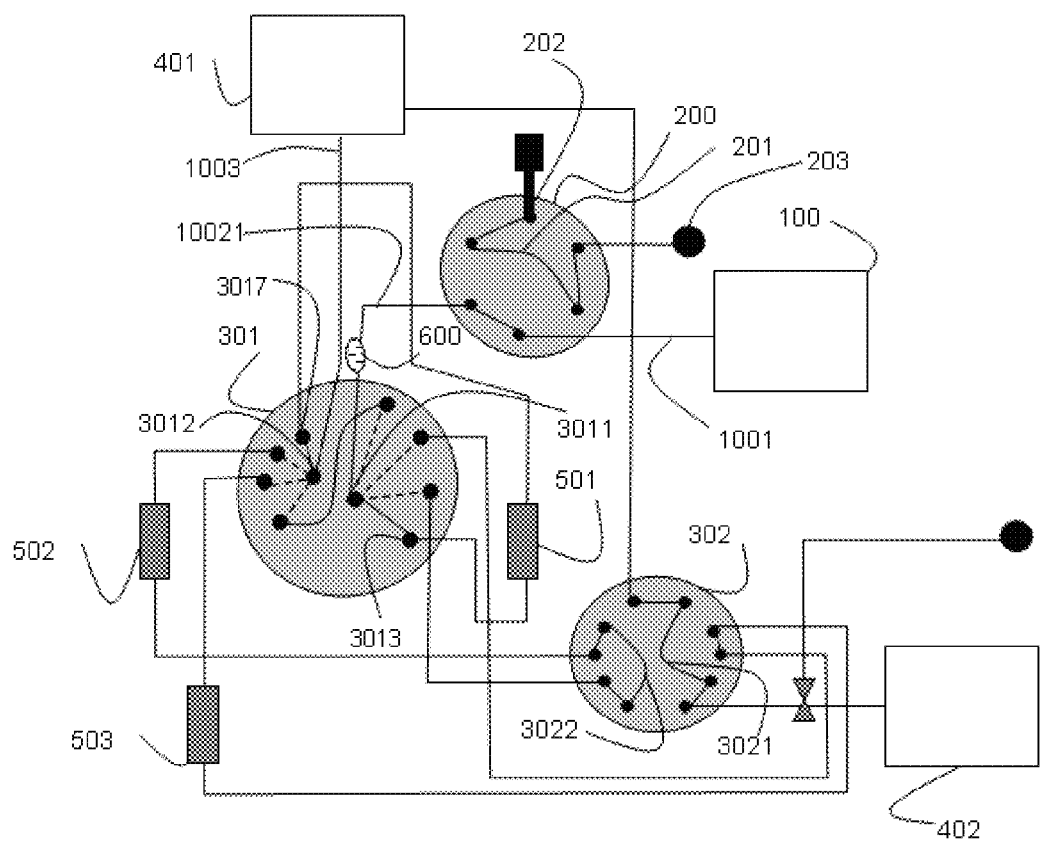
FIG. 4A is a flow diagram of the devices of the multidimensional chromatographic assembly of FIG. 1, showing an example of the individual valve positions for the first dimension run; the analyte is on route to the first dimension chromatographic medium.
Figure 4B:
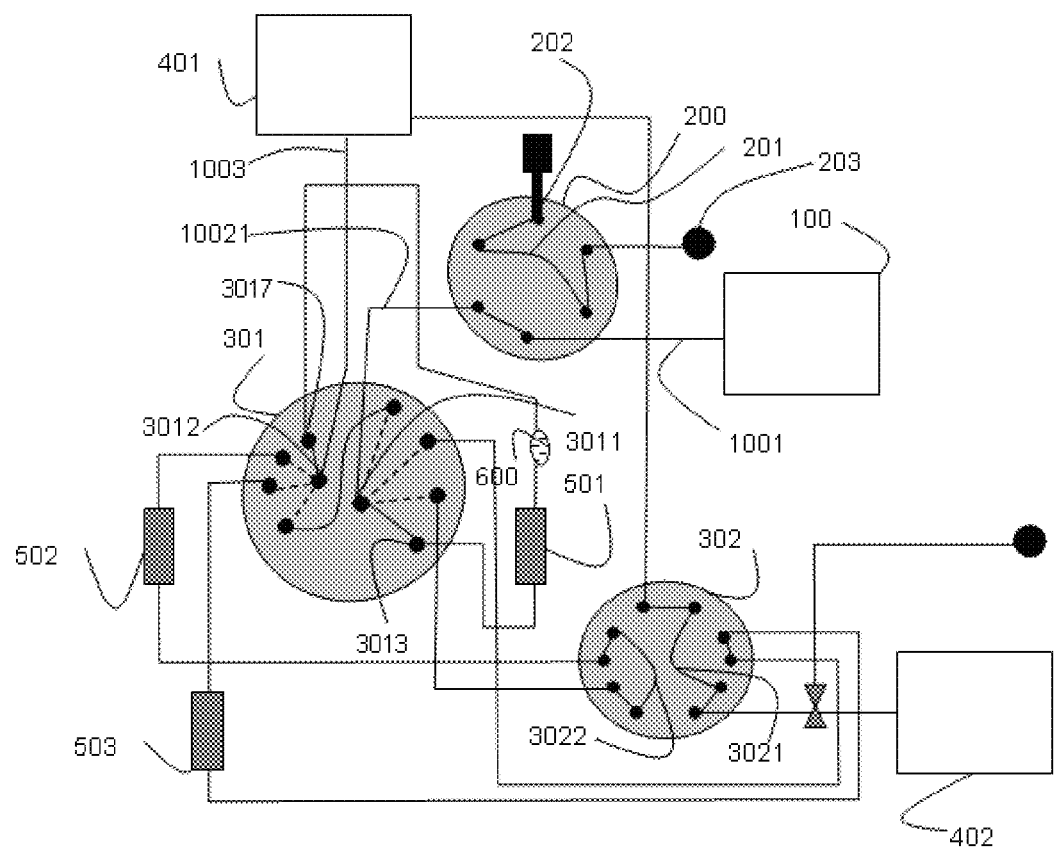
FIG. 4B is a flow diagram of the devices of the multidimensional chromatographic assembly of FIG. 1, showing an example of the individual valve positions for the first dimension run; the analyte is shown at the flow-path downstream of the first dimension chromatographic medium.
Figure 4C:
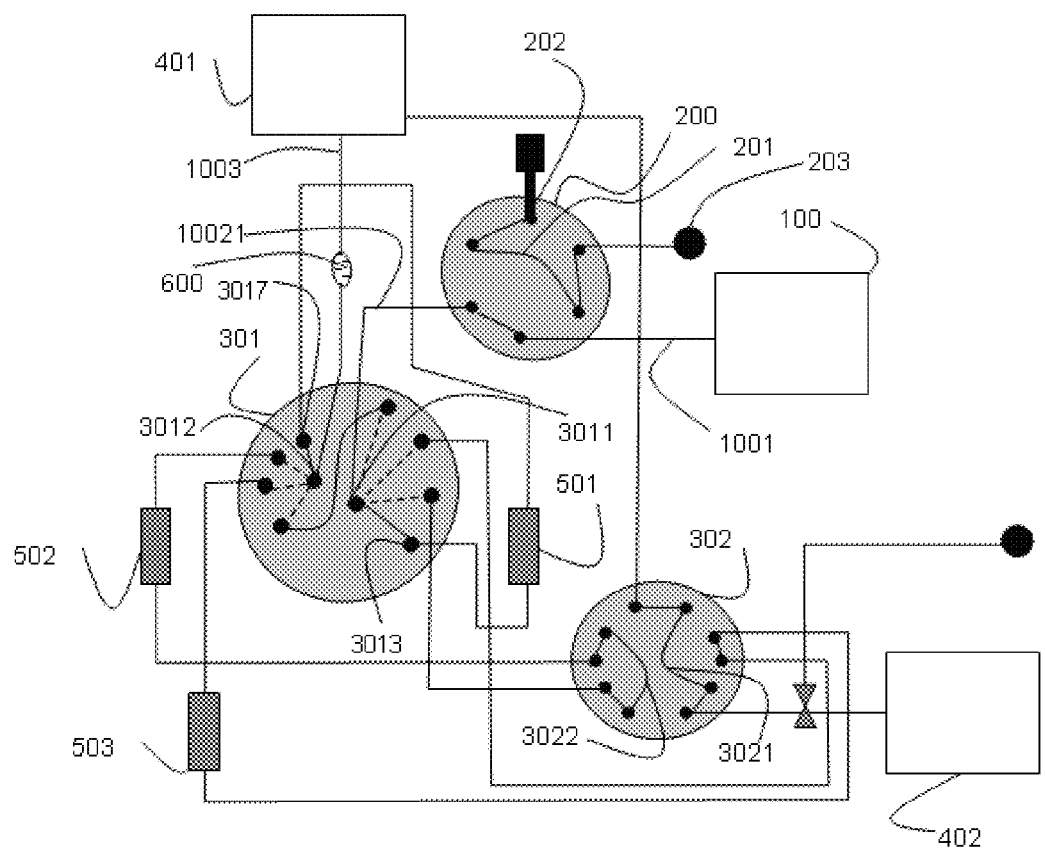
FIG. 4C is a flow diagram of the devices of the multidimensional chromatographic assembly of FIG. 1, showing an example of the individual valve positions for the first dimension run; the analyte is shown at the flow-path on route to the detector assembly.
Figure 4D:
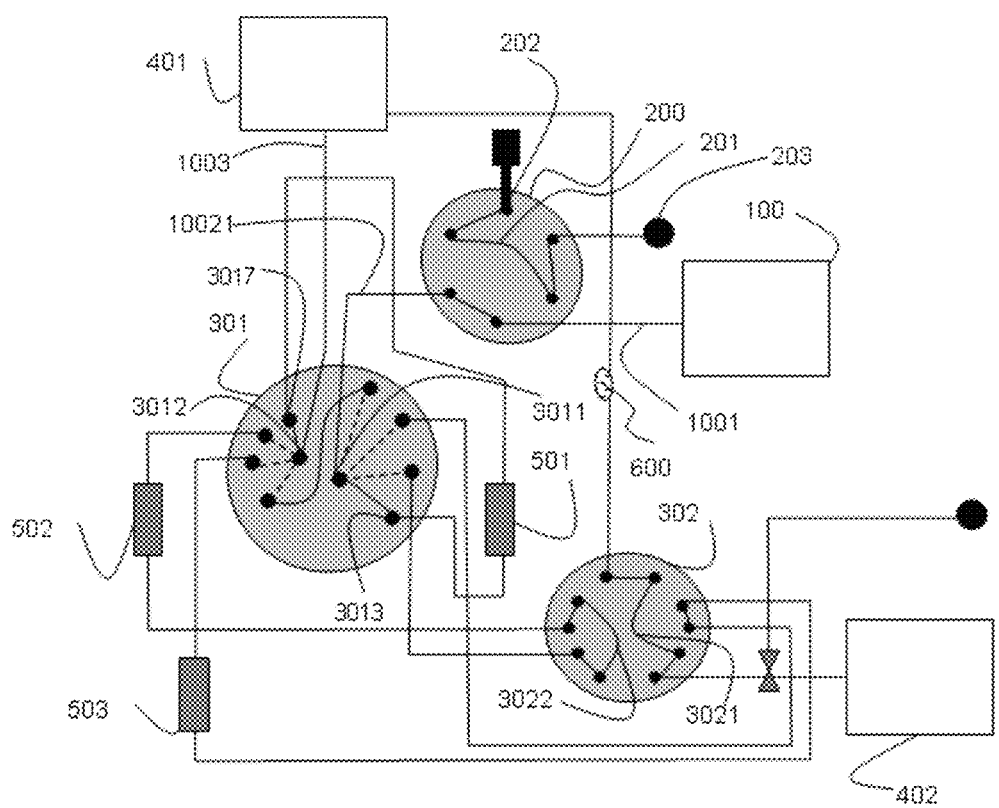
FIG. 4D is a flow diagram of the devices of the multidimensional chromatographic assembly of FIG. 1, showing an example of the individual valve positions for the first dimension run; the analyte is shown at the flow-path downstream of the detector assembly on route to the fluid channeling device (e.g., a loop selector device)
Figure 4E:
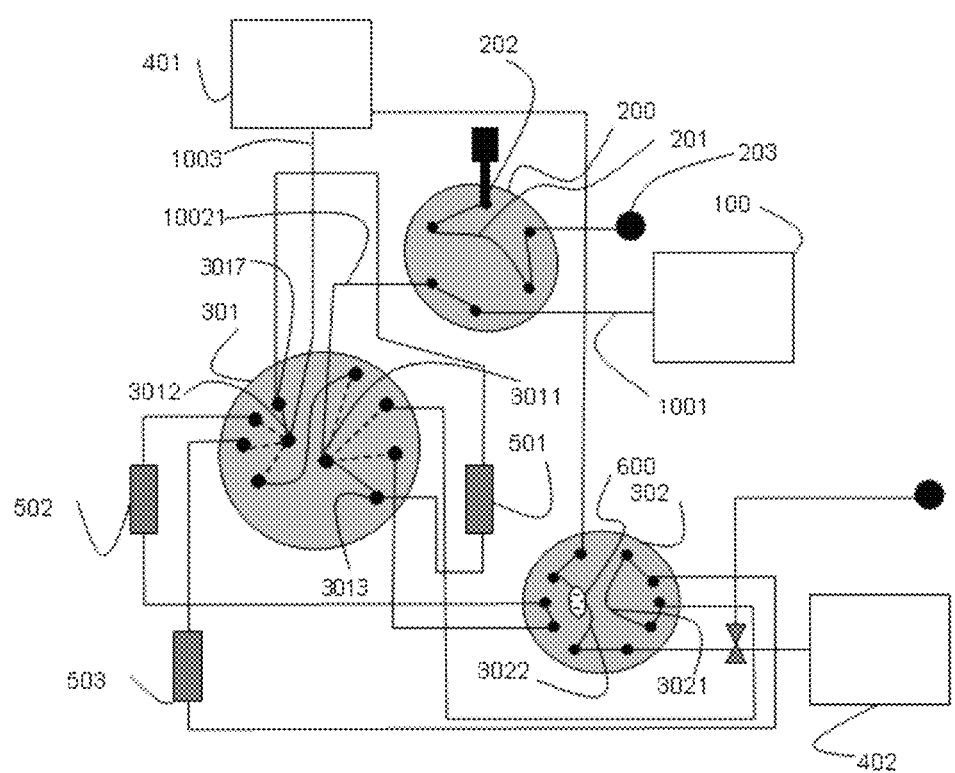
FIG. 4E is a flow diagram of the devices of the multidimensional chromatographic assembly of FIG. 1, showing an example of the individual valve positions for the first dimension run; the analyte is in the selected fluid holding device (e.g., a loop) mounted on the fluid channeling device (e.g., the loop selector device)
Figure 4F:
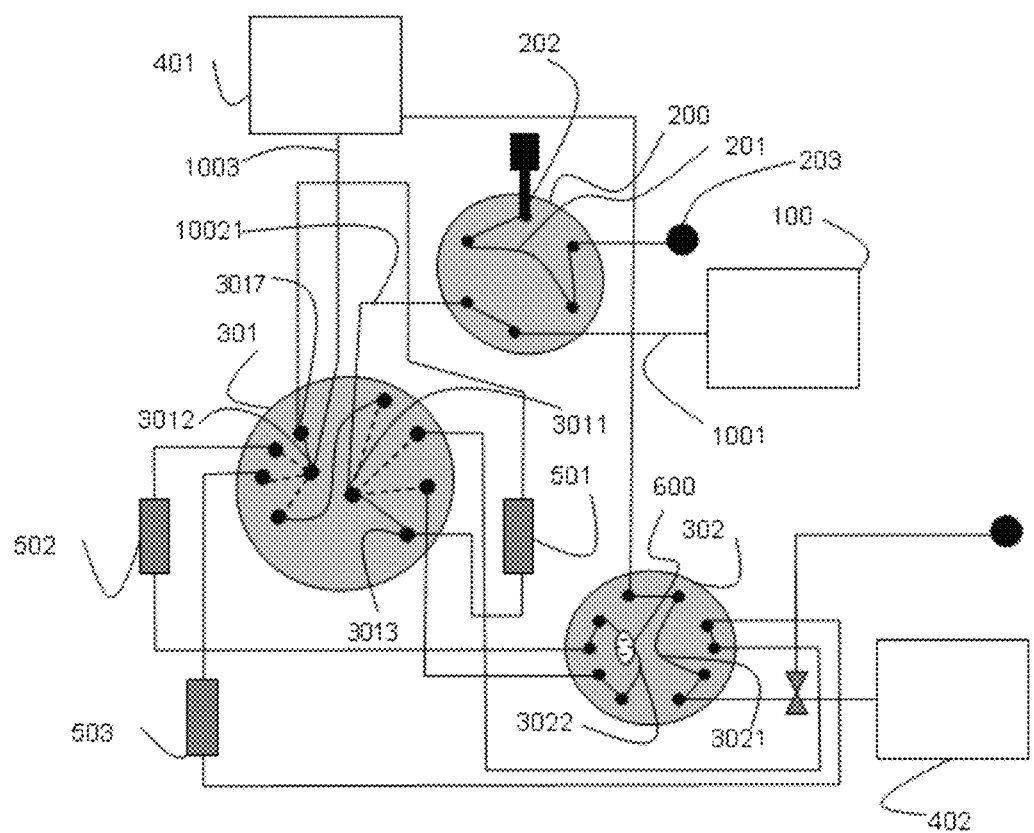
FIG. 4F is a flow diagram of the devices of the multidimensional chromatographic assembly of FIG. 1, showing an example of the individual valve positions for the continuation of the first dimension run; the analyte is parked in the loop while the remainder of the first dimension run is being completed.

Referring to FIGS. 4A to 4F, in the embodiment shown in FIG. 4A, the analyte 600 is shown upstream of the path selector device 301 and downstream of the injector 200 and is on route to the chromatographic medium 501 via the path selector device 301. The analyte 600 is chromatographed in the chromatographic medium 501 (FIG. 4B) and is allowed to flow into the detector device 401 (FIG. 4C). FIG. 4D shows the location of the analyte 600 after its first dimension analysis and the analyte is on route to flow into the loop selector device 302. The loop selector device 302 is movable to direct the targeted analyte 600 into the loop 3022 (shown in FIG. 4E), and to isolate the analyte 600 (shown in FIG. 4F) in the loop 3022. The movement of the valve is controlled by external instruction(s) (e.g., codes, commands, programs, signals, switches or a combination of these). In some embodiments, the loop selector device 302 is rotated based on time or the eluent volume. In alternate embodiments, signals for the valve rotation are generated based on the detector response. In other embodiments, signals are generated from the computer 1000 (FIG. 1) following an algorithm operating on the basis of the response obtained from the detector assembly 400.

Figure 5A:
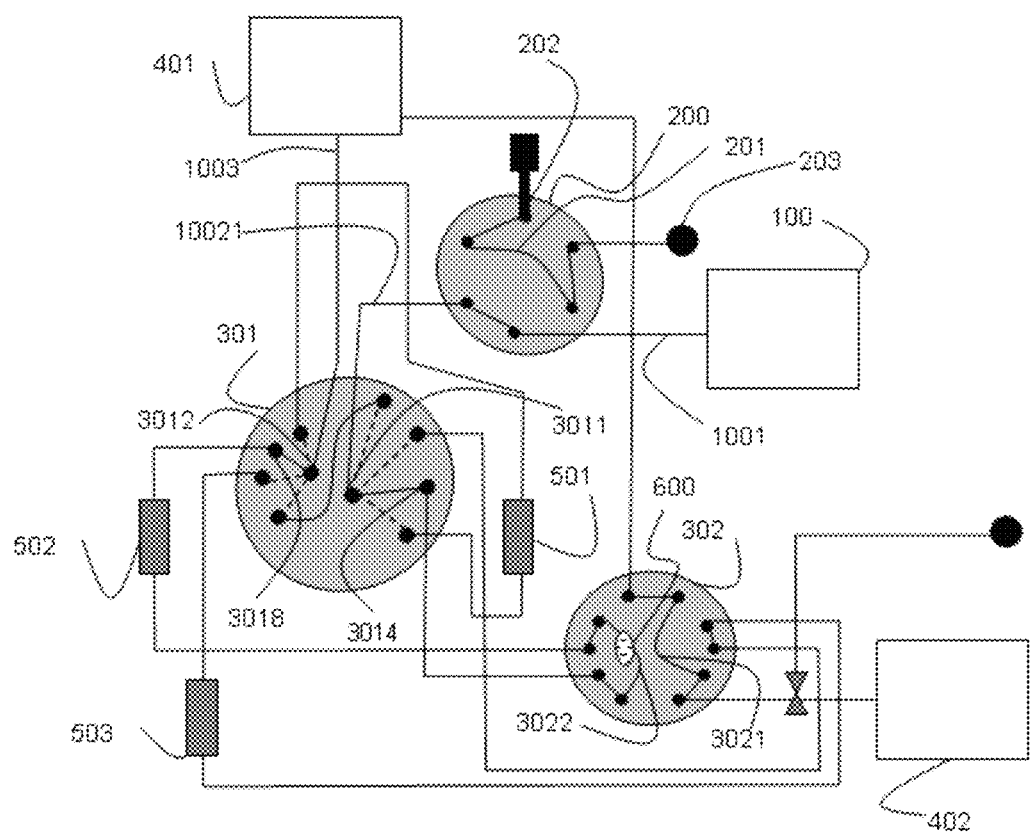
FIG. 5A is a flow diagram of the devices of the multidimensional chromatographic assembly of FIG. 1, showing an example of the individual valve positions for the second dimension run; the analyte is in fluid communication with the loop and the second dimension chromatographic medium.
Figure 5B:
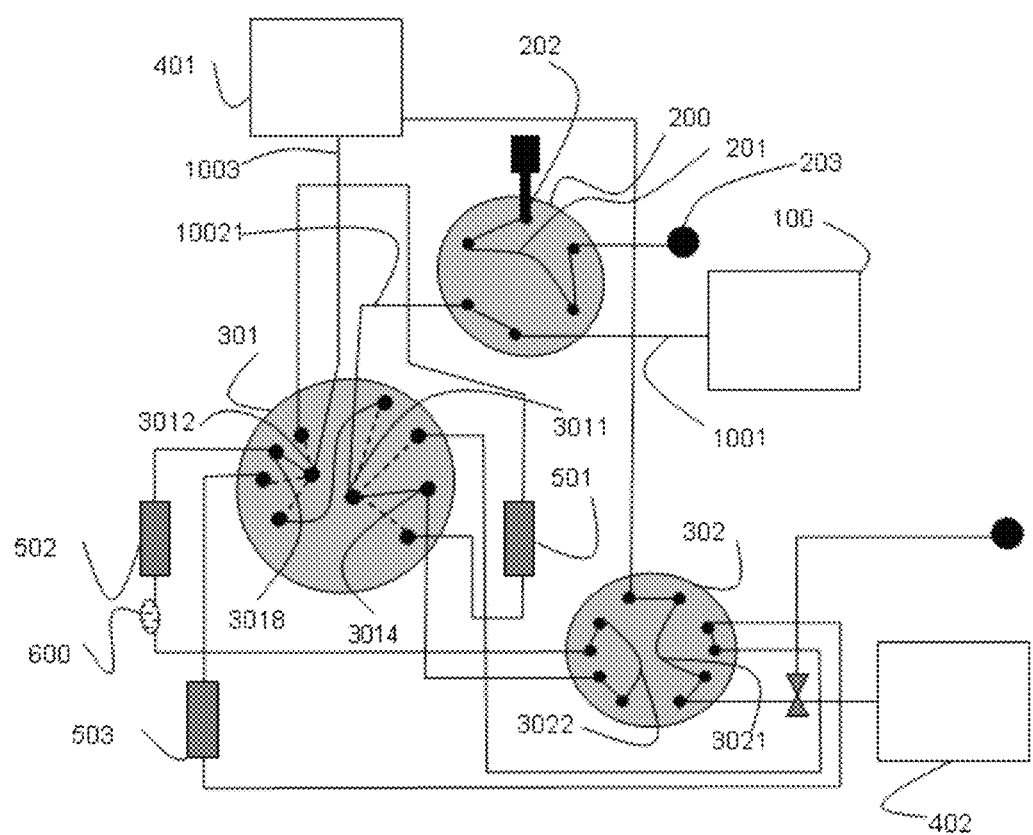
FIG. 5B is a flow diagram of the devices of the multidimensional chromatographic assembly of FIG. 1, showing an example of the individual valve positions for the second dimension run; the analyte is on route to the second dimension chromatographic medium.
Figure 5C:
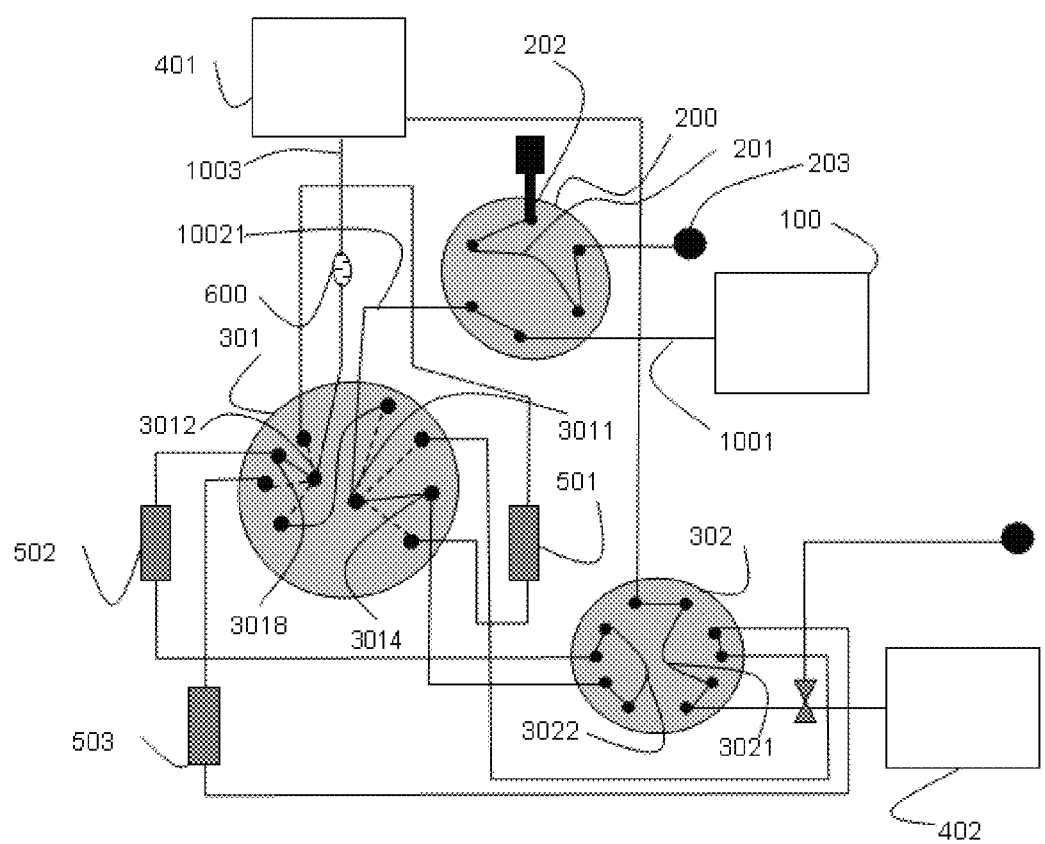
FIG. 5C is a flow diagram of the devices of the multidimensional chromatographic assembly of FIG. 1, showing an example of the individual valve positions for the second dimension run; the analyte is on route to the detector assembly for the second dimension analysis.
Figure 5D:
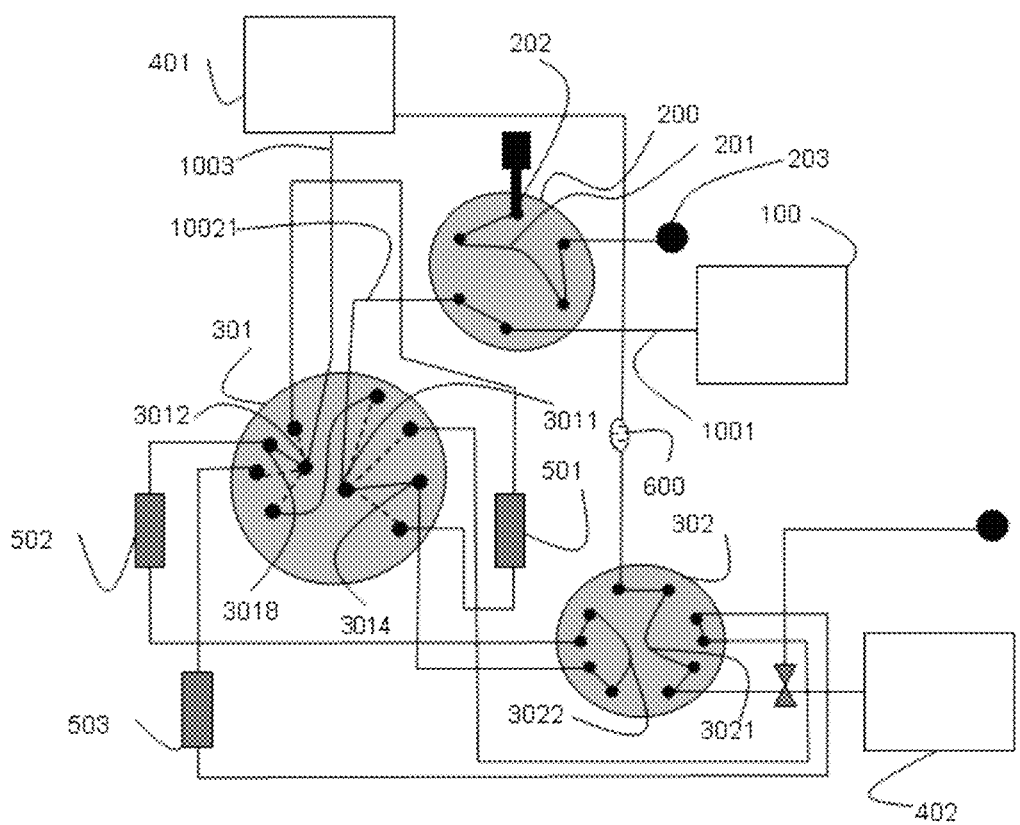
FIG. 5D is a flow diagram of the devices of the multidimensional chromatographic assembly of FIG. 1, showing an example of the individual valve positions for the second dimension run; the analyte is on route to the fluid channeling device (e.g., the loop selector device) for the third dimension run.
Figure 5E:
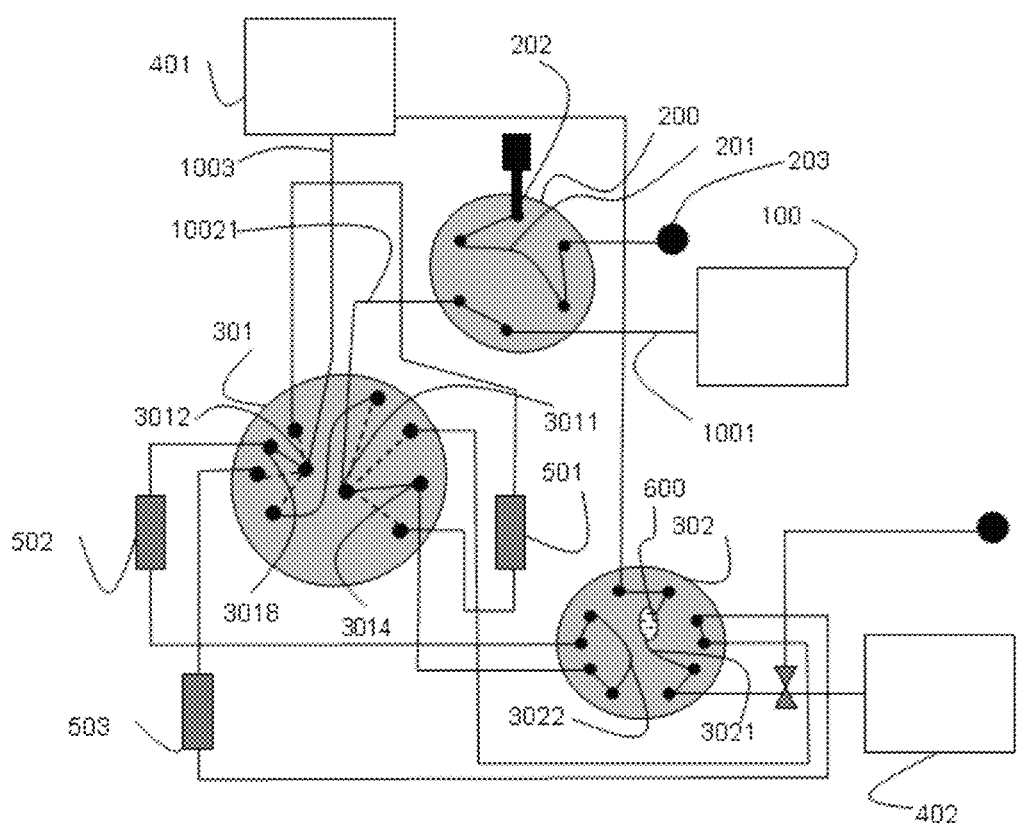
FIG. 5E is a flow diagram of the devices of the multidimensional chromatographic assembly of FIG. 1, showing an example of the individual valve positions for the second dimension run; the analyte is in the loop of choice for the third dimension run.
Figure 5F:
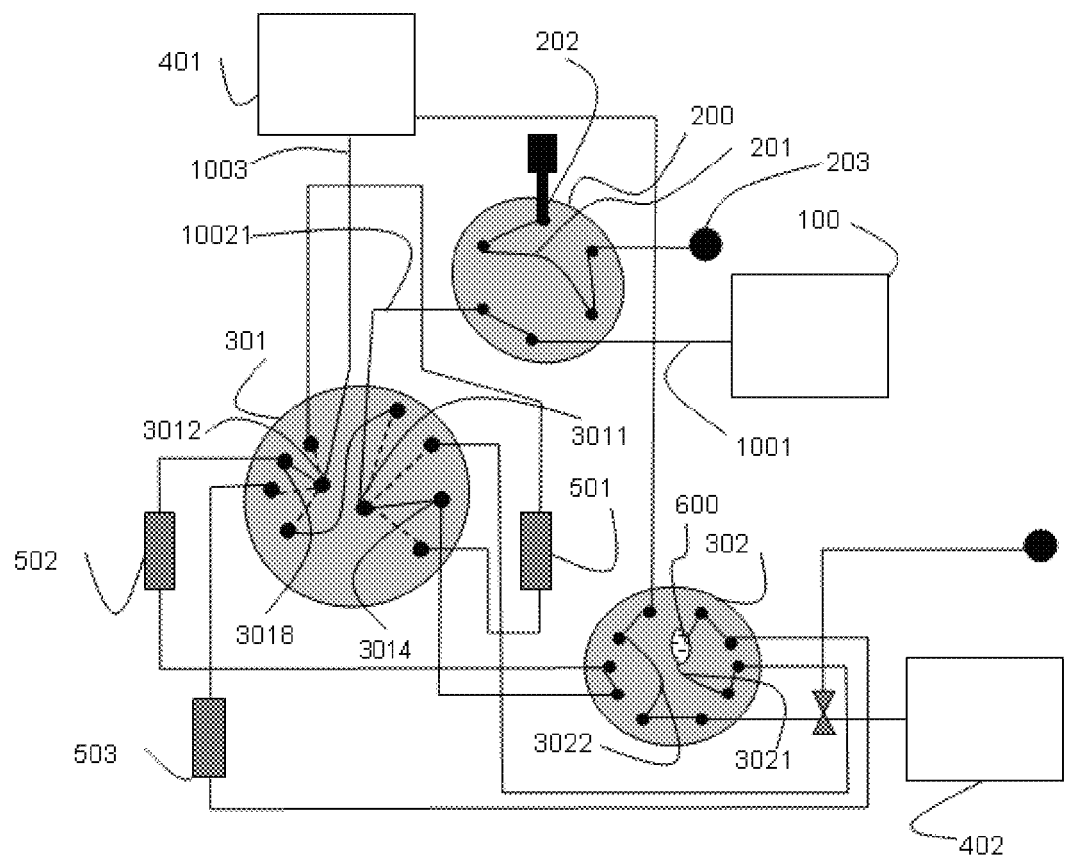
FIG. 5F is a flow diagram of the devices of the multidimensional chromatographic assembly of FIG. 1, showing an example of the individual valve positions for the continuation of the second dimension run; the analyte is parked in the loop for the third dimension run.
Figure 6A:
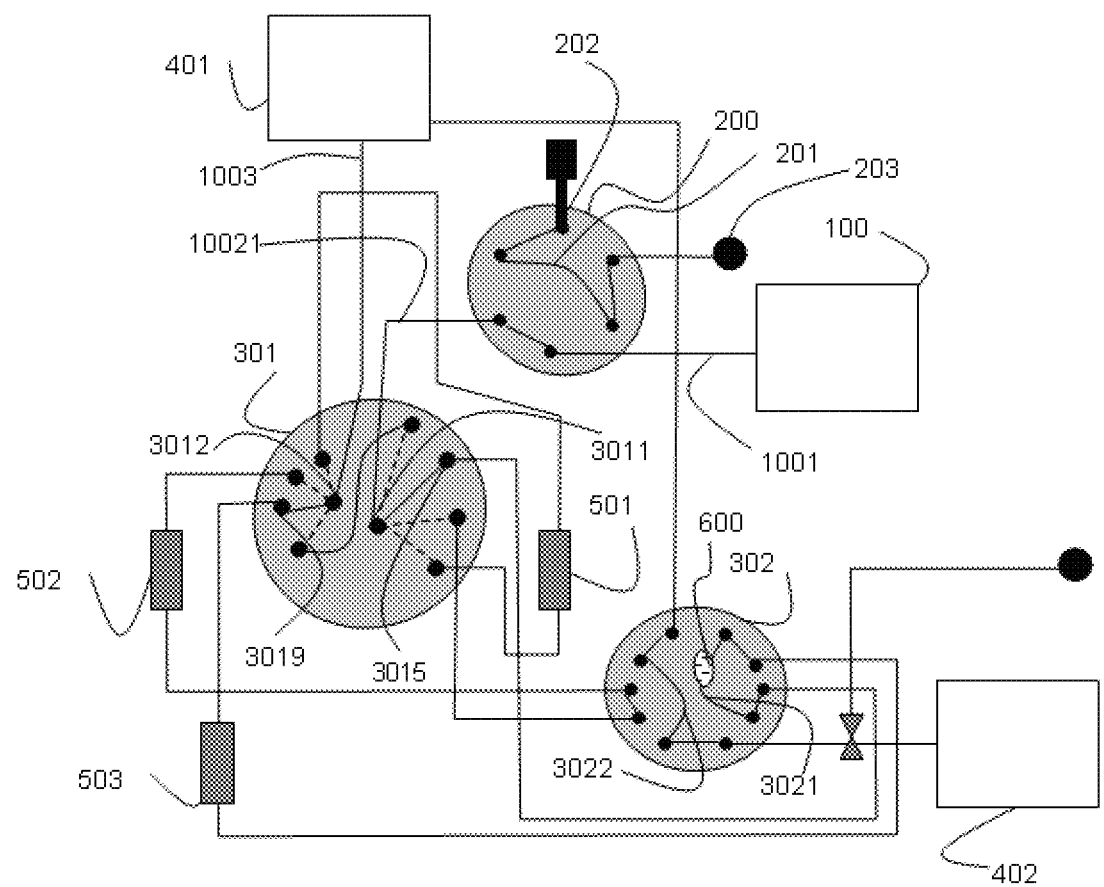
FIG. 6A is a flow diagram of the devices of the multidimensional chromatographic assembly of FIG. 1, showing an example of the individual valve positions for the third dimension run; the analyte is in fluid communication with the pump module and the third dimension chromatographic medium.
Figure 6B:
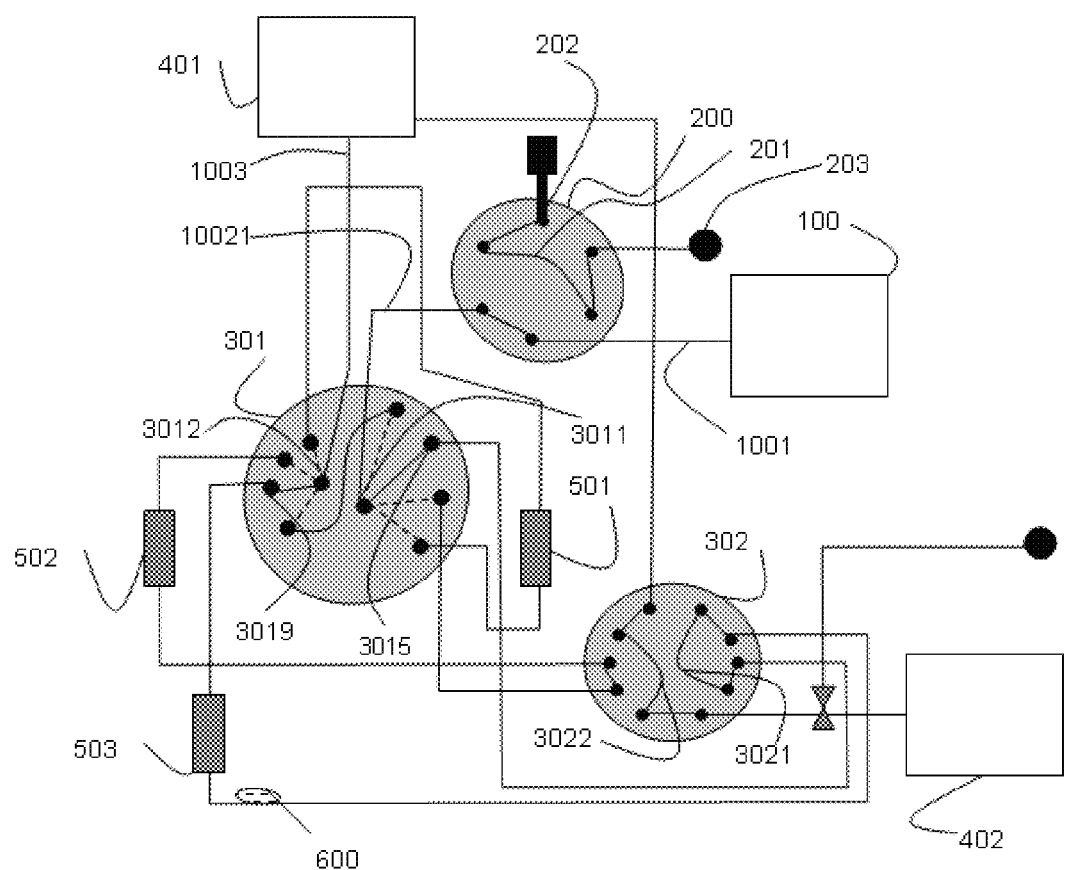
FIG. 6B is a flow diagram of the devices of the multidimensional chromatographic assembly of FIG. 1, showing an example of the individual valve positions for the third dimension run; the analyte is on route to the third dimension chromatographic medium.
Figure 6C:
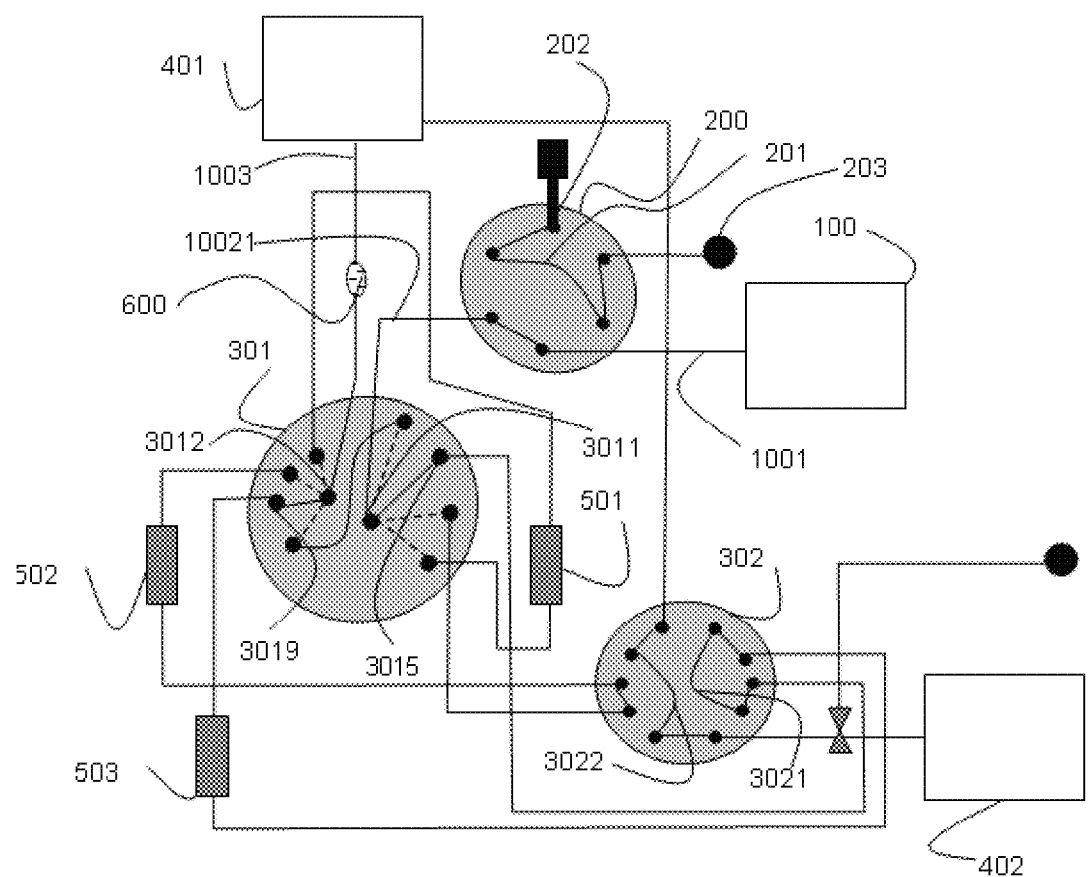
FIG. 6C is a flow diagram of the devices of the multidimensional chromatographic assembly of FIG. 1, showing an example of the individual valve positions for the third dimension run; the analyte is on route to the detector assembly after the third dimension run.
Figure 6D:
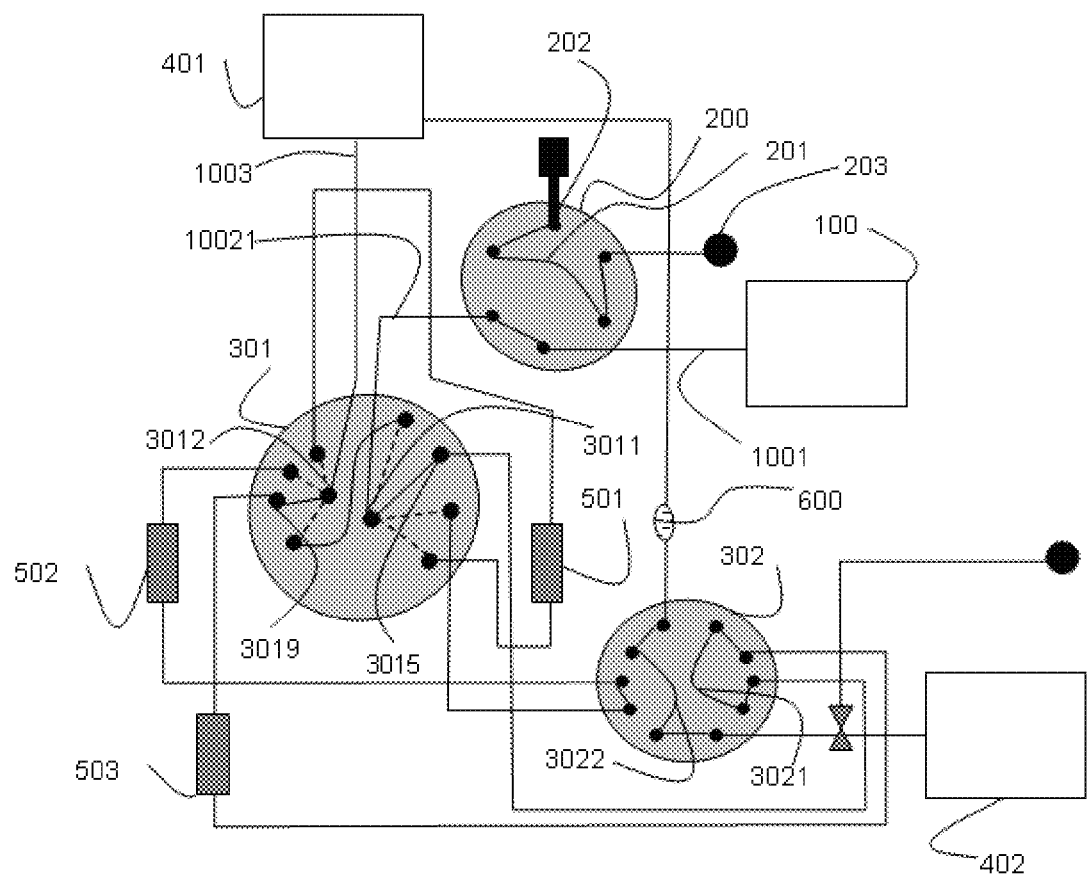
FIG. 6D is a flow diagram of the devices of the multidimensional chromatographic assembly of FIG. 1, showing an example of the individual valve positions for the third dimension run; the analyte is on route to the fluid channeling device (e.g., the loop selector device)
Figure 6E:
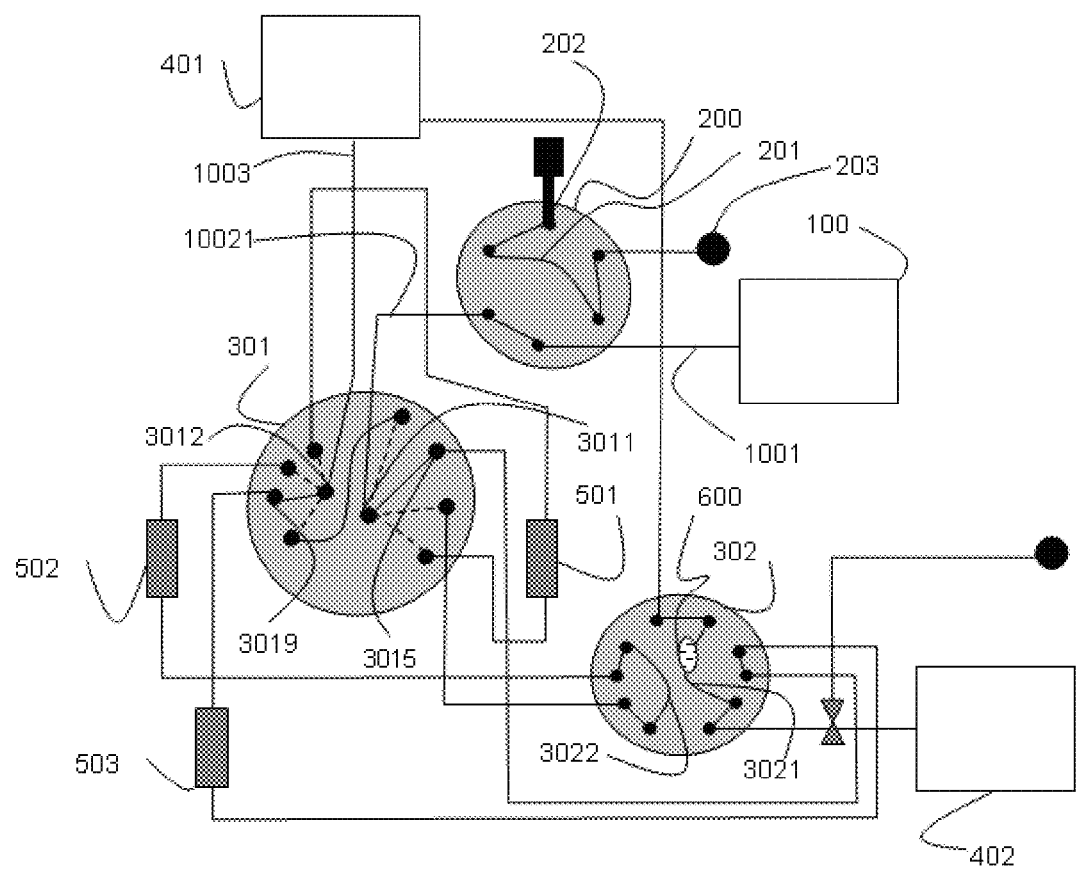
FIG. 6E is a flow diagram of the devices of the multidimensional chromatographic assembly of FIG. 1, showing an example of the individual valve positions for the third dimension run; the analyte is in the loop mounted on the fluid channeling device (e.g., the loop selector device)
Figure 6F:
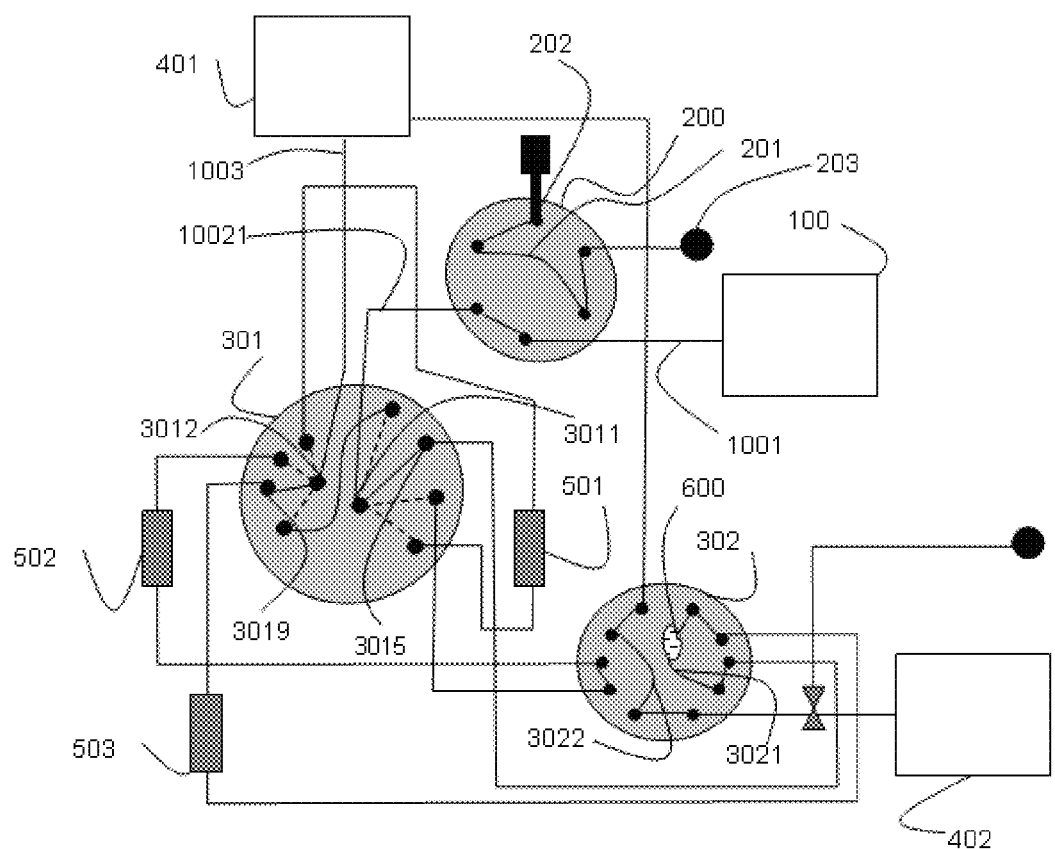
FIG. 6F is a flow diagram of the devices of the multidimensional chromatographic assembly of FIG. 1, showing an example of the individual valve positions for the subsequent run; the analyte is in fluid communication with the pump module and the third dimension chromatographic medium.
Figure 6G:
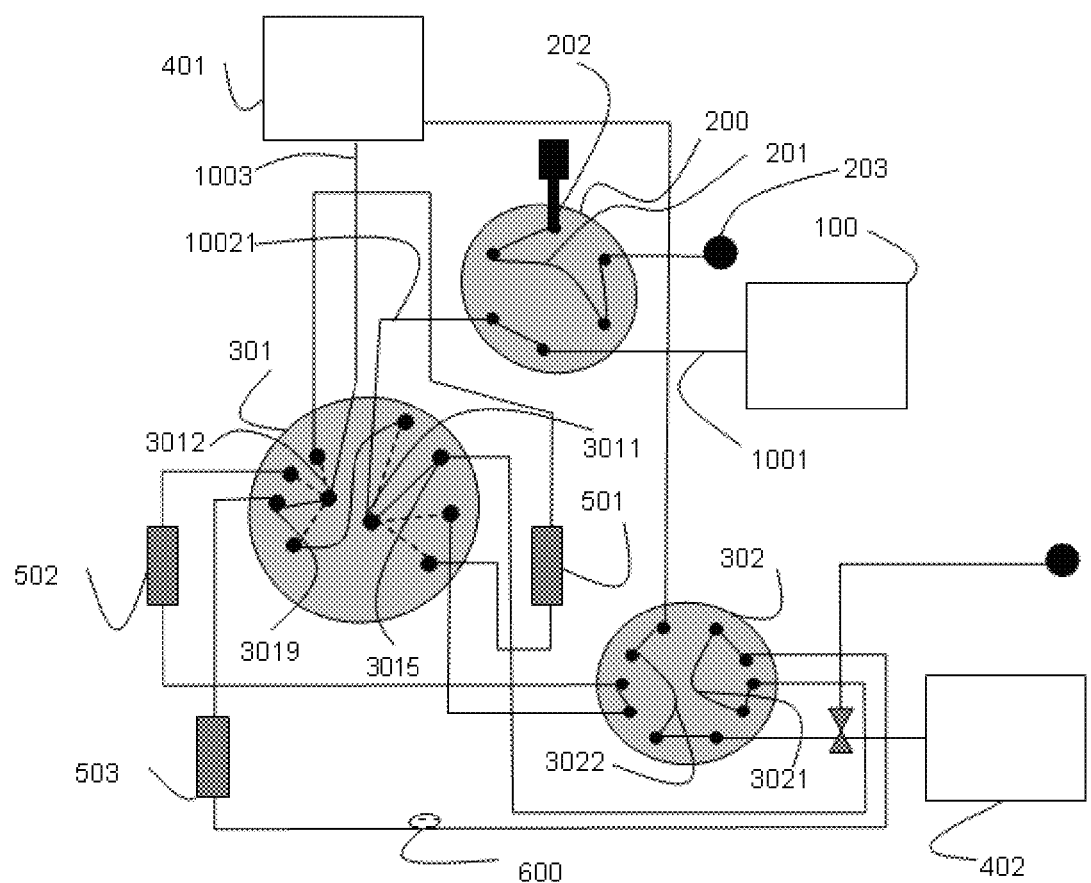
FIG. 6G is a flow diagram of the devices of the multidimensional chromatographic assembly of FIG. 1, showing an example of the individual valve positions for the subsequent run; the analyte is on route to a chromatographic medium for subsequent analysis.
Figure 6H:
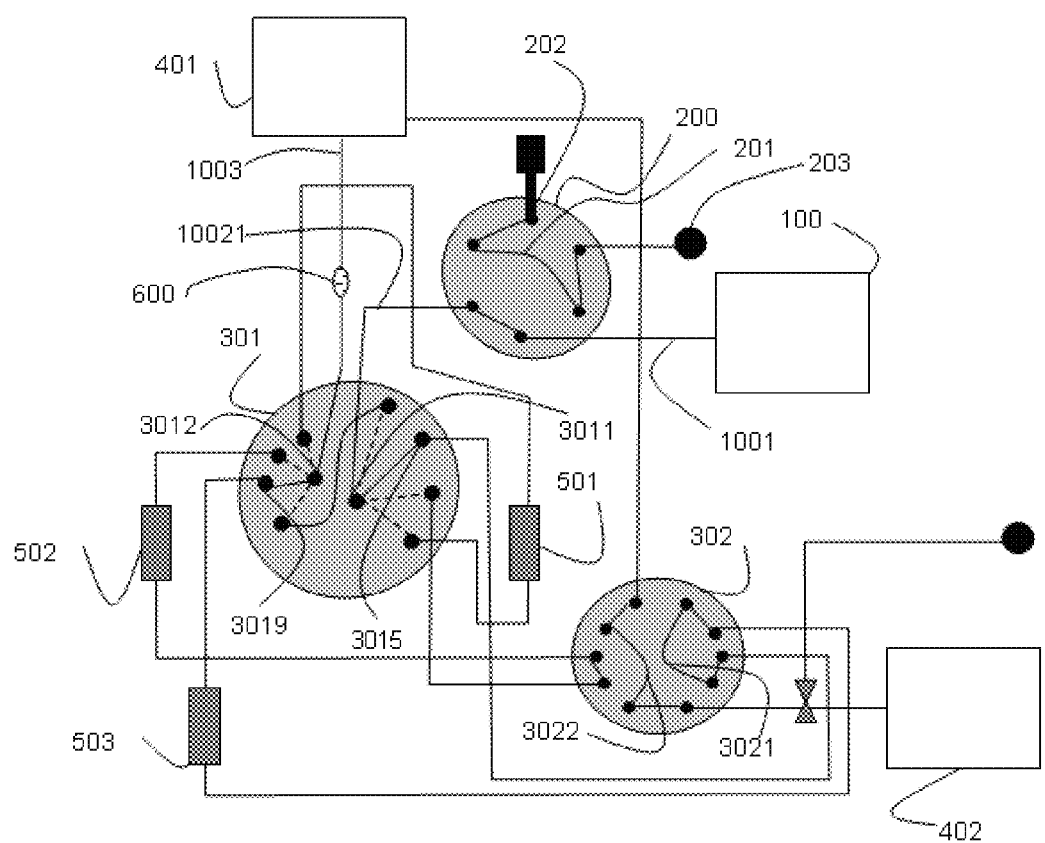
FIG. 6H is a flow diagram of the devices of the multidimensional chromatographic assembly of FIG. 1, showing an example of the individual valve positions for the subsequent run; the analyte is on route to the detector assembly for subsequent analysis.
Figure 6I:
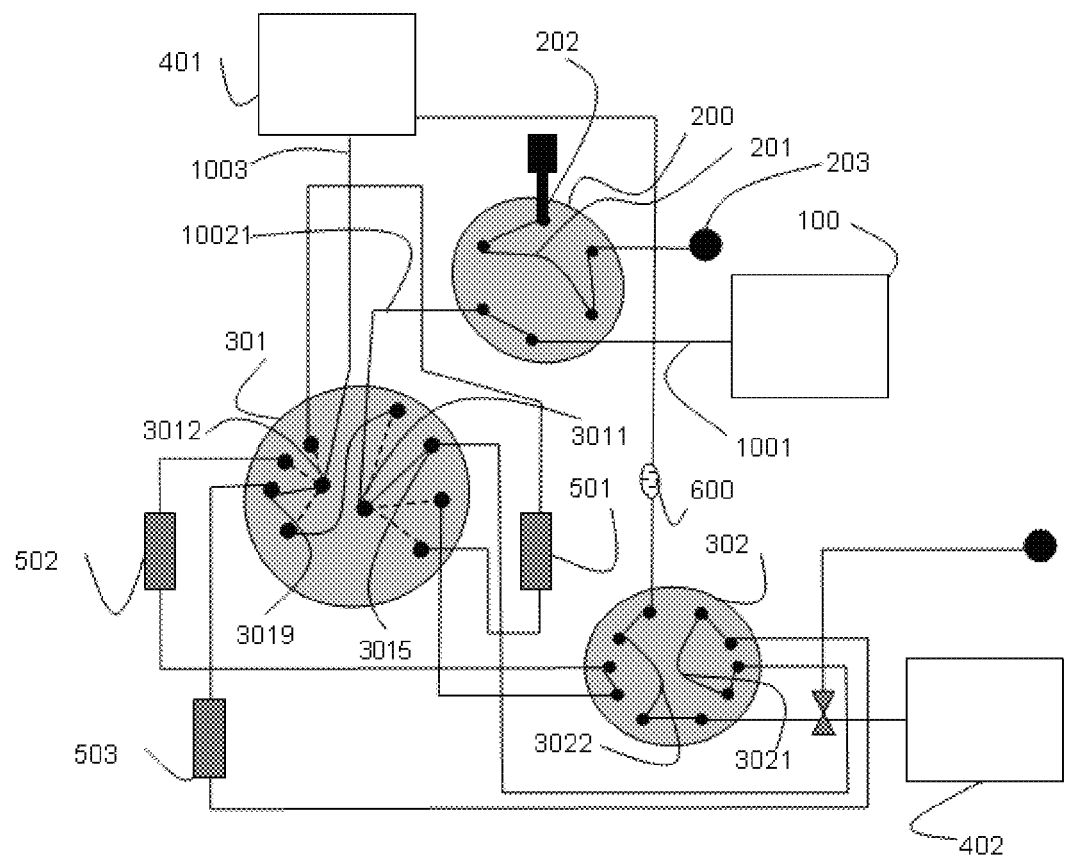
FIG. 6I is a flow diagram of the devices of the multidimensional chromatographic assembly of FIG. 1, showing an example of the individual valve positions for the subsequent run; the analyte is shown in the path downstream of the detector assembly and upstream of the fluid channeling device (e.g., the loop selector device); the analyte can be diverted for further analysis (e.g., fourth dimension) or sent to waste.

In the embodiment shown in FIG. 5A, the pump module 100 is in fluid communication with the loop 3022 and a part of the chromatographic media array 500 (specifically, 502).

As can be seen in FIGS. 5B to 5F, the chromatographed analyte 600 can be moved through the chromatographic media 502 into the detector device 401 and be deposited in the loop 3021 by the similar mechanism as described.

In use, the loop selector device 302 may be periodically moved from the one position to the other and then from the second position back to the first position, in order to store at least a portion of the targeted peak 600 for further analysis.

The path selector and the loop selector device 300 (e.g., 301 and 302) may be systematically moved in order for the targeted peak to be re-circulated until all aspects of the analysis are judged complete (FIG. 6A-6I).

In some embodiments, additional path selector and loop selector devices of type 300 can be introduced between the chromatographic media array 500 (e.g., 502 or 503) and the loop selector device (e.g., 302) to further extend the dimensions of the chromatographic media array 500.

The invention claimed is:

1. A method for performing a multidimensional analysis comprising:
   a) priming at least one flow-path with suitable fluids using a pump for chromatographic runs in each dimension;
   b) injecting at least a portion of an analyte into an injector;
   c) flowing at least a portion of the injected analyte from the injector using the pump;
   d) chromatographing the at least a portion of the injected analyte using a chromatographic medium;
   e) analyzing at least a portion of the chromatographed analyte using a detector;
   f) diverting at least a portion of the chromatographed analyte of step d) to a second chromatographic medium for re-analysis using the pump and a loop selector;
   g) chromatographing the diverted portion of step f) using the second chromatographic medium;
   h) analyzing at least a portion of the chromatographed analyte of step g) using the detector;
   i) isolating the at least a portion of the chromatographed analyte of step g); and
   j) diverting the at least a portion of the chromatographed analyte of step g) to the second chromatographic medium or a third chromatographic medium for a higher-dimension analysis using the loop selector and the pump.

2. The method of claim 1, further comprising the step of:
   k) isolating the at least a portion of the chromatographed analyte of step g) and diverting the at least a portion of the chromatographed analyte of step g) back to either the second or the third chromatographic medium for re-analysis.

3. The method of claim 1 or 2, wherein step f), j) or k) comprises programming the loop selector to divert at least a portion of any of the chromatographed analytes based on a pre-set time during the chromatographic runs or a pre-set volume of at least one chromatographic eluent.

4. The method of claim 1 or 2, wherein step f), j) or k) comprises analyzing the analyte in the detector and programming the loop selector to divert at least a portion of any of the chromatographed analytes based on a pre-coded algorithm.

5. The method of claim 4, wherein step f), j) or k) comprises programming the loop selector to divert at least a portion of any of the chromatographed analytes to the second or the third chromatographic medium based on a response from the detector.

6. The method of claim 1 or 2, wherein step f), i), j) or k) comprises analyzing the analyte in the detector and operating the loop selector to divert at least a portion of any of the chromatographed analytes by procedures implemented by a source other than a computer.

7. The method of claim 2, further comprising the step of:
l) analyzing the analyte in the detector and programming the loop selector to re-circulate at least a portion of the chromatographed analyte from step (k) through either the second or the third chromatographic medium for an unrestricted number of times.

* * * * *